United States Patent [19]
Gillio

[11] Patent Number: 5,798,489
[45] Date of Patent: Aug. 25, 1998

[54] DETACHABLE STETHOSCOPE

[76] Inventor: Robert G. Gillio, 2001 Pine Dr., Lancaster, Pa. 17601

[21] Appl. No.: 669,736

[22] Filed: Jun. 26, 1996

[51] Int. Cl.[6] .................................................. A61B 7/02
[52] U.S. Cl. ........................................................ 181/131
[58] Field of Search .................................. 181/131, 137; 381/67

[56] References Cited

U.S. PATENT DOCUMENTS

| | | |
|---|---|---|
| 2,807,328 | 9/1957 | Gould . |
| 3,867,925 | 2/1975 | Ersek . |
| 4,064,965 | 12/1977 | Brown . |
| 4,497,124 | 2/1985 | Olive . |
| 4,997,055 | 3/1991 | Grady . |
| 5,650,598 | 7/1997 | Abelson ................................ 181/131 |

*Primary Examiner*—Khanh Dang
*Attorney, Agent, or Firm*—Kenyon & Kenyon

[57] ABSTRACT

A stethoscope having a separable connection in the sound conducting tube permits the removal and attachment of various sound receiving portions. The connection has a first coupler attached to one free end of the sound conducting tube, and a second coupler attached to the other free end of the sound conducting tube. Each of the couplers is attached to the outer surface of the tube to avoid altering the inner diameter of the tubes in the vicinity of the connection. Maintaining the original diameter of the inner tube surface prevents adverse effects on the transmitted sound as it passes through the connected tube sections and reduces wear at the tube end. The first and second couplers are held together by suitable mechanical or magnetic attachment means that permit quick and easy separation of the couplers.

8 Claims, 6 Drawing Sheets

DETACHABLE STETHOSCOPE

FIELD OF THE INVENTION

The present invention relates generally to a stethoscope and more particularly to a stethoscope having a separable connection in the sound conduction tube for the attachment of a variety of sound receiving portions.

BACKGROUND OF THE INVENTION

Stethoscopes are generally used to listen to sounds within the body and generally include a flexible sound conducting tube connected at one end to a sound receiving portion which detects the sounds and at the other end to a headset unit that transmits the detected sounds to the user.

The repeated use of stethoscopes on a number of different patients raises concern for the possible risk of infection. To overcome this problem, Ulert (U.S. Pat. No. 4,867,268) discloses a sanitary stethoscope having a specially designed stethoscope head adapted to hold a disposable diaphragm. Ulert does not disclose how the diaphragm is connected to the flexible sound conducting tube. Nor does Ulert suggest that the diaphragm may be detachable from the sound conducting tube. Brown (U.S. Pat. No. 4,064,965) discloses a stethoscope in which the sound pick-up diaphragm could be separated and left in the patients's room. To permit removal of the sound pick-up diaphragm, the headset unit is connected to the flexible tube with a series if connector plugs attached to a "Y"-shaped yoke connecting member. Thus, when the sound pick-up diaphragm is separated from the headset, the entire length of the flexible tube is also separated from the headset. In addition, the variation of inner diameters from the connectors to the tubes may adversely affect sound transmission from the diaphragm to the earplugs. Grady (U.S. Pat. No. 4,997,055) discloses a stethoscope having a plurality of disposable sound receiving sensors. The disposable sensors are connected to the common sound conduction tube through a valve housing unit. The valve housing unit connects to the sound conducting tubes by inserting the ends of the unit into the open ends of the tubes. This type of connection stretches the tube and may lead to excessive wear at the tube ends and an unreliable seal between the unit and the tubes. In addition, the connection distorts the tube and may adversely affect sound transmission from the sensors to the eartips.

For situations in which a patient requires frequent monitoring, Ersek (U.S. Pat. No. 3,867,925) discloses an expendable stethoscope having a disposable section which includes a bell means and a flexible conduit means. The disposable section is adapted to enable surface attachment of the bell means to the skin of a patient. The headpiece is connected to the disposable portion by inserting a rigid adapter portion of the headpiece into the tip portion of an adapter on the disposable portion. Thus, the bell means is removed from the head piece by disconnecting the entire flexible conduit from the head piece.

The variation in inner diameter of the sound conducting tube from the sound receiving portion to the headset may cause distortion in the transmitted sound and adversely affect the ability of the user to interpret the received sound. In addition, repeated insertions of connectors into the ends of the flexible sound conducting tube can cause degradation of the tube end with associated degradation in the connection. And, for stethoscopes with multiple connections, the potential for distortion of the transmitted sound increases with the number of connections.

None of the stethoscopes disclosed in the prior art provides a connection in the flexible tubing that permits attachment of various sound receiving portions, reduces wear on the ends of the flexible tube, provides reliable connection and minimizes adverse effects on sound transmission from the sound receiving portion to the head set.

SUMMARY OF THE INVENTION

The present invention solves these problems by providing a stethoscope having a separable connection in the sound conducting tube to permit the removal and attachment of various sound receiving portions. The connection has a first coupler attached to the outer surface of one free end of the sound conducting tube, and a second coupler attached to the outer surface of the other free end of the sound conducting tube. When the couplers are connected, the free ends of the sound conducting tubes meet so that the inner diameter of the tube is substantially constant between the sound receiving portion and the headset. Each of the couplers is attached to the outer surface of a tube in order to avoid altering the inner diameter of the tubes in the vicinity of the connection. This also reduces wear on the tubes ends since tubes are not stretched to accommodate any connectors. By maintaining the original diameter of the inner surface of the tube, the transmitted sound is not adversely affected as it passes through the connected tube sections, and the tube ends are subjected to less wear. The first and second couplers are held together by suitable mechanical or magnetic attachment means that permit quick, easy and reliable connection and separation of the couplers.

The present invention provides a high quality stethoscope which is suitable for general physician use. In addition, the stethoscope provides a detachable portion which can be retained by a patient or disposed of when used in infectious environments.

DETAILED DESCRIPTION

Figure 1:
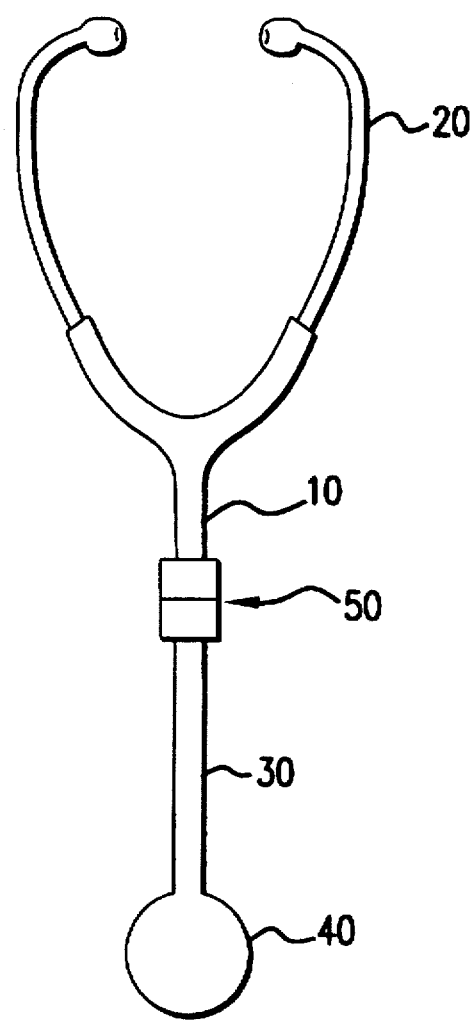
FIG. 1 is a plan view of a stethoscope having a tube connector in the sound conducting tube in accordance with the present invention.

FIG. 1 shows a stethoscope 1 having an upper sound conducting tube 10 connected to a headset 20. A lower sound conducting tube 30 is connected to a sound receiving portion 40. The upper sound receiving tube 10 and the lower sound receiving tube 30 are connected at a tube connector 50.

Figure 2:
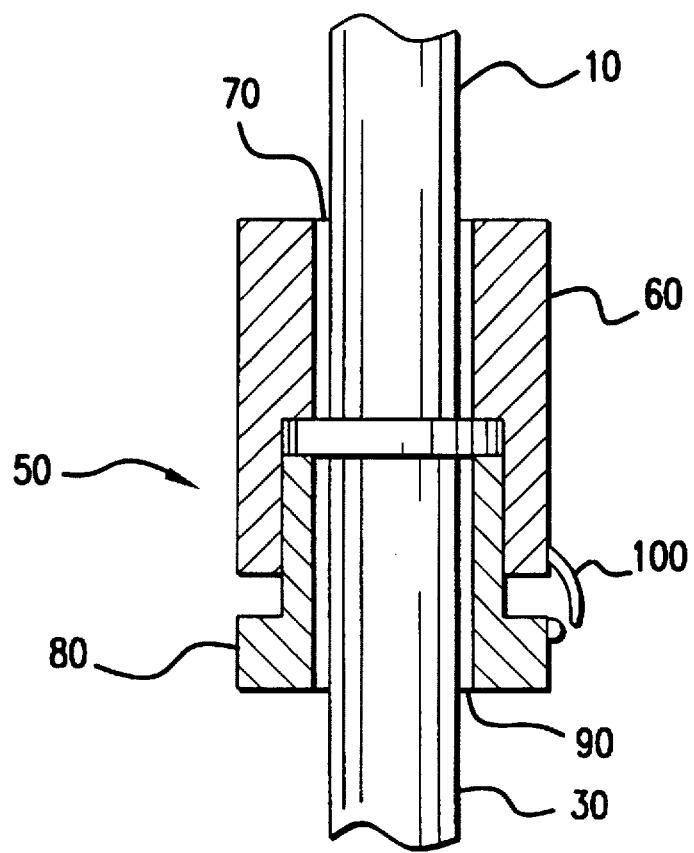
FIG. 2 is a section view of a tube connector in the sound conducting tube of the stethoscope of FIG. 1.

As shown in FIG. 2, the tube connector 50 includes a female coupler 60 attached by an adhesive 70 to the outer surface of the upper sound conducting tube 10. A male coupler 80 is attached to the outer surface of the lower sound conducting tube 30 by adhesive 90. The couplers are mated and secured by mechanical means such as a latch 100. When the couplers 60, 80 are secured, the free ends of the upper and lower sound conducting tubes 10, 30 are mated with a secure and non-constricting seal so that sound traveling from the sound receiving portion 40 to the headset 20 is not adversely affected as it passes through the tube connector 50. Attachment of the coupler to the outer surface of the tube also reduces wear on the tube ends that would normally occur in devices in which connectors are inserted into the tube ends.

Figure 3:
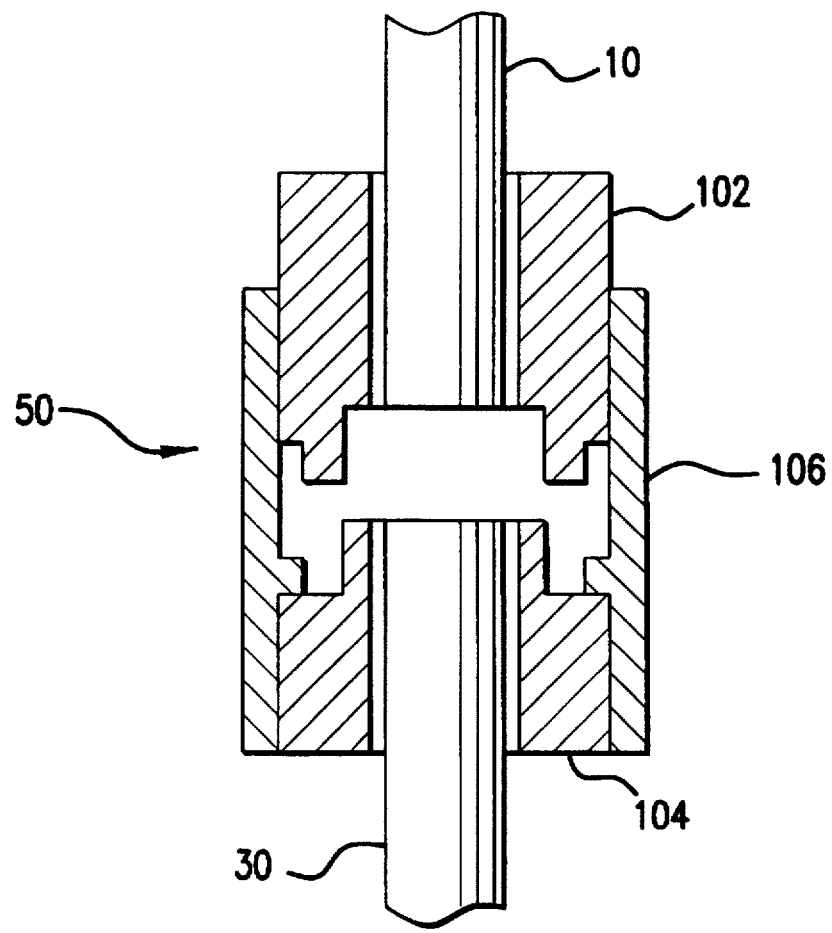
FIG. 3 is a section view of another embodiment of the tube connector of the present invention.

FIG. 3 shows another embodiment of the invention wherein the tube connector 50 includes a female coupler 102 attached to the outer surface of the upper sound conducting tube 10 and a male coupler 104 attached to the outer surface of the lower sound conducting tube. The couplers 102, 104 are detachably interconnected so that the free ends of the upper and lower sound conducting tubes 10, 30 are mated with a secure and non-constricting seal so that sound traveling from the sound receiving portion 40 to the headset 20 is not adversely affected as it passes through the tube connector 50, and the tube ends are subject to less wear. An acoustic insulator 106 is attached to one of the couplers and extends over the joint between the two couplers 102, 104 to decrease the amount of external sound transmitted to the interior of the sound conducting tubes 10, 30. The acoustic insulator can be made from any suitable material which can reduce sound transmission, including plastic and rubber.

Figure 4:
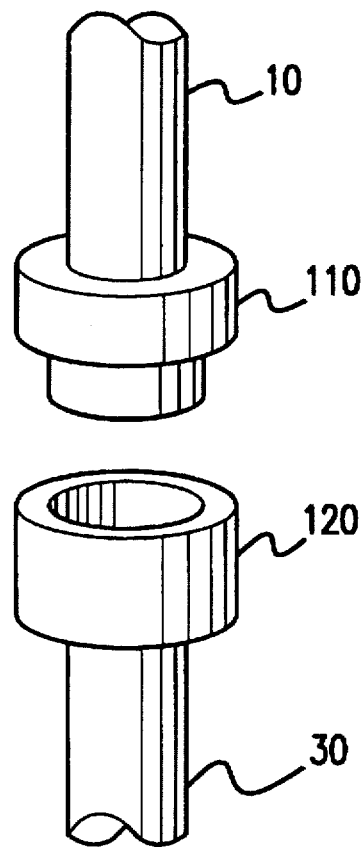
FIG. 4 is a perspective view of still another embodiment of a tube connector of the present invention.

FIG. 4 shows another embodiment of the invention wherein a first magnetic coupler 110 is adhesively attached to the outer surface of the free end of the upper sound conducting tube 10. A second magnetic coupler 120 is attached to the outer surface of the free end of the lower sound conducting tube 30. Each magnetic connector 110, 120 is oppositely charged so that the couplers form an intimate seal when connected.

Figure 5:
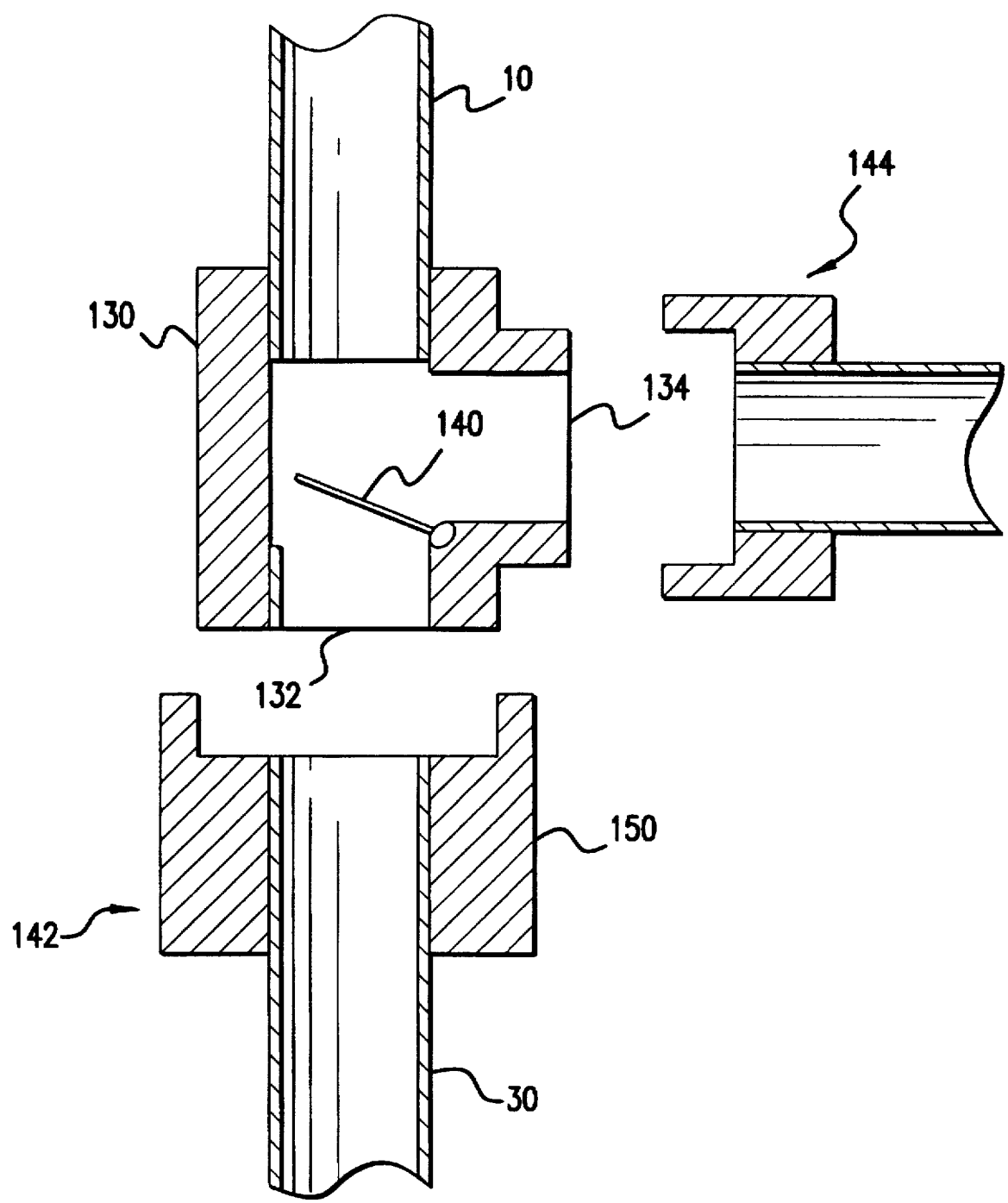
FIG. 5 is a section view of a tube connector adapted to accommodate two sound receiving portions.

FIG. 5 illustrates another embodiment of the present invention wherein a first coupler 130 is attached to the outer surface of the upper sound conducting tube 10. The first coupler 130 is configured to include two passageways 132, 134. Sound transmission is directed through either passageway by a valve arrangement 140 that can selectively block either passageway. Use of a swing valve is illustrated in FIG. 5. However, a variety of well known valve arrangements may be used. Various sound receiving portions 142, 144 can be connected at the openings of either or both of the passageways 132, 134 in the first coupler 130. One of the connected sound receiving portions may be attached to a lower sound conducting tube 30 as illustrated in FIGS. 24. In this case, the lower sound conducting tube 30 has a coupler 150 attached to the outer surface of the tube, and the coupler 150 is configured to mate with the first coupler 130. It is also possible to attach sound receiving portions from devices such as electronic stethoscopes, microphones, temperature sensors and ultrasound probes. When these types of sound receiving portions are used, the first coupler has at least one portion of the coupler adapted to connect to the particular sound receiving portion.

In each of the embodiments shown in FIGS. 2–4, the attachments of the couplers to the sound conducting tubes provides a tight seal but does not constrict the inner diameters of the sound conducting tubes. This reduces wear on the tube ends and permits sound to travel from the sound receiving portion to the headset through a sound conducting tube having a substantially constant inner diameter. In addition, although the couplers illustrated in FIGS. 2–4 are shown in association with respective upper or lower sound conducting tubes, it should be understood that the positions of the male and female couplers can be exchanged without departing from the scope of the present invention. For example, referring to FIG. 2, couplers 60 and 80 can be attached to the outer surfaces of the lower and upper sound conducting tubes 30 and 10, respectively. Each of the couplers shown in FIGS. 2, 3 and 5 may be made of a variety of materials including metal and plastics as long as the material is sufficiently strong to maintain the connection and has sufficient rigidity to avoid constriction of the sound conducting tubes. In addition, the magnetic couplers of FIG. 4 may be made entirely from magnetic material or may be a combination of magnetic material with a variety of other materials such as metal or plastic. Any suitable adhesive may be used to attach the couplers to the sound conducting tubes.

Although the stethoscope of the present invention is schematically illustrated in FIG. 1 with a typical diaphragm-type sound receiving bell, the lower sound conducting tube may alternatively be connected to an electronic stethoscope or other devices such as doppler instruments, temperature sensors, ultrasound probes, microphones, speakers or any other device designed to transmit an auditory signal.

Figure 6:
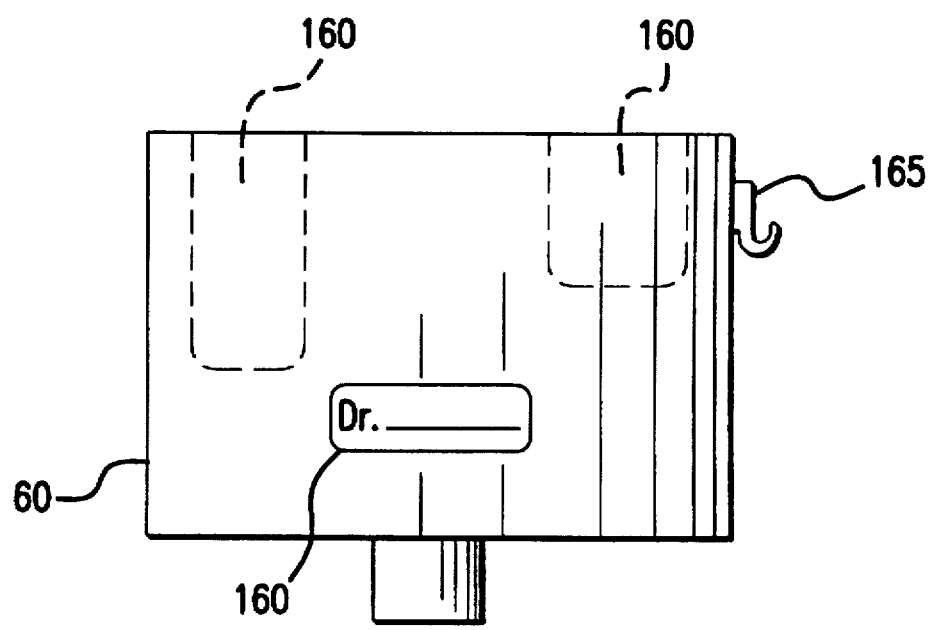
FIG. 6 is a front view of a coupler adapted to hold accessory items.

In addition, a coupler may be configured to conveniently hold accessory items. For example, as shown in FIG. 6, the coupler 60 may have recesses 160 and hook 165 to accomodate items such as a badge, nameplate, writing instrument, microcomputer, calculator, pager or other communications device, or a variety of other small items that a user may wish to have readily available. Also, an accessory item such as a dispenser for latex or plastic covers or condoms for the stethoscope may be attached to the coupler. Such a dispenser would be particularly advantageous when the physician has a detachable stethoscope, but the patient does not have their own patient portion. In such case, the physician may dispense a cover or condom that is used to cover the listening end of the stethoscope prior to use on a patient.

What is claimed is:

1. A stethoscope device comprising:
    an upper assembly including a headset and an upper sound conducting tube connected to the headset, the upper sound conducting tube having a free end and an outer surface;
    a lower assembly including a sound receiving portion and a lower sound conducting tube, the lower sound conducting tube having a free end and an outer surface; and
    a tube connector, wherein the tube connector detachably interconnects the free ends of the upper and lower sound conducting tubes and is attached to the outer surfaces of the upper and lower sound conducting tubes and wherein said tube connector includes a first male coupler sealably attached to the outer surface of the free end of one of the upper or lower sound conducting tubes and a second female coupler sealably attached to the outer surface of the free end of the other upper or lower sound conducting tube.

2. The device of claim 1, further comprising a sound insulation layer attached to the outer surface of at least one of the couplers and extending over a joint formed by the connection of the free ends of the upper and lower sound conducting tubes.

3. A stethoscope device comprising:
    an upper assembly including a headset and an upper sound conducting tube connected to the headset, the upper sound conducting tube having a free end and an outer surface;
    a lower assembly including a sound receiving portion and a lower sound conducting tube, the lower sound conducting tube having a free end and an outer surface; and
    a tube connector, wherein the tube connector detachably interconnects the free ends of the upper and lower sound conducting tubes and is attached to the outer surfaces of the upper and lower sound conducting tubes, said tube connector including a first coupler sealably attached to the outer surface of the free end of one of the upper or lower sound conducting tubes and a second coupler sealably attached to the outer surface of the free end of the other of the upper or lower sound conducting tube wherein the first and second couplers are magnetic and oppositely charged.

4. A stethoscope device comprising:

an upper assembly including a headset and an upper sound conducting tube connected to the headset, the upper sound conducting tube having a free end and an outer surface;

a lower assembly including a sound receiving portion and a lower sound conducting tube, the lower sound conducting tube having a free end and an outer surface;

a tube connector, wherein the tube connector detachably interconnects the free ends of the upper and lower sound conducting tubes and is attached to the outer surfaces of the upper and lower sound conducting tubes, said tube connector including a first coupler sealably attached to the outer surface of the free end of one of the upper or lower sound conducting tubes and a second coupler sealably attached to the outer surface of the free end of the other of the upper or lower sound conducting tube; and a sound insulation layer attached to the outer surface of at least one of the couplers and extending over a joint formed by the connection of the free ends of the upper and lower sound conducting tubes.

5. A stethoscope device comprising:

an upper assembly including a headset and an upper sound conducting tube connected to the headset, the upper sound conducting tube having a free end and an outer surface;

a lower assembly including a sound receiving portion and a lower sound conducting tube, the lower sound conducting tube having a free end and an outer surface; and a tube connector, wherein the tube connector detachably interconnects the free ends of the upper and lower sound conducting tubes and is attached to the outer surfaces of the upper and lower sound conducting tubes and wherein the tube connector further comprises:

a first coupler sealably attached to the outer surface of the free end of the upper sound conducting tube, the first coupler having at least two passageways; and a valve disposed in the first coupler, the valve being adapted to selectively block each of the passageways;

wherein the first coupler is adapted to releasably connect with the lower assembly at each opening of the at least two passageways.

6. The device of claim 5, further comprising at least one additional lower assembly.

7. The device of claim 2, wherein the first and second couplers are magnetic and oppositely charged.

8. The device of claim 7, wherein the coupler attached to the free end of the upper sound conducting tube includes retaining means to accommodate accessory items.

* * * * *